United States Patent
Svensson

(10) Patent No.: US 6,670,378 B2
(45) Date of Patent: Dec. 30, 2003

(54) METHOD OF TREATING PARKINSON'S DISEASE

(75) Inventor: Kjell A. Svensson, Portage, MI (US)

(73) Assignee: Pharmacia & Upjohn Company, Kalamazoo, MI (US)

(*) Notice: Subject to any disclaimer, the term of this patent is extended or adjusted under 35 U.S.C. 154(b) by 0 days.

(21) Appl. No.: 10/054,758

(22) Filed: Nov. 13, 2001

(65) Prior Publication Data

US 2002/0169187 A1 Nov. 14, 2002

Related U.S. Application Data

(63) Continuation-in-part of application No. 09/976,688, filed on Oct. 12, 2001.
(60) Provisional application No. 60/289,431, filed on May 8, 2001.

(51) Int. Cl.[7] ............................................. A61K 31/451
(52) U.S. Cl. ...................................................... 514/317
(58) Field of Search ................................. 514/317, 331, 514/408, 428, 429

(56) References Cited

U.S. PATENT DOCUMENTS

| 5,462,947 A | 10/1995 | Svensson et al. ............ 514/317 |
| 5,594,024 A | 1/1997 | Svensson et al. ............ 514/429 |

FOREIGN PATENT DOCUMENTS

| WO | WO 99/03470 | 1/1999 |
| WO | 00/03714 | * 1/2000 |

OTHER PUBLICATIONS

Ekesbo et al., NeuroReport, 8(11), 2567–2570 (Jul. 28, 1997).*

* cited by examiner

*Primary Examiner*—Phyllis G. Spivack
(74) *Attorney, Agent, or Firm*—Flynn, Thiel, Boutell, Tanis, P.C.

(57) ABSTRACT

A method of preventing the development of dyskinesias in patients being treated for Parkinson's Disease requires the administration of a pharmacologically effective amount of a substituted phenylazacycloalkane to the patient. The patient is treated for Parkinson's disease by administering at least one dopamine agonist to the patient and by the transplantation of dopamine neurons into the patient's brain.

10 Claims, 5 Drawing Sheets

METHOD OF TREATING PARKINSON'S DISEASE

This is a continuation-in-part of Ser. No. 09/976,688, filed Oct. 12, 2001 and claims benefit of No. 60/289,431 filed May 8, 2001.

FIELD OF THE INVENTION

The present invention is directed to methods for preventing the development of and treating dyskinesias in patients being treated for Parkinson's disease utilizing substituted phenylazacycloalkanes and dopamine agonists.

BACKGROUND OF THE INVENTION

Parkinson's disease is pathologically associated with a degeneration within the nuclear masses of the extrapyramidal system and the characteristic loss of melanin-containing cells from the substantia nigra and a corresponding reduction in dopamine levels in the corpus striatum. A conventional method of treating Parkinson's disease involves the administration of a dopamine agonist to a patient suffering from this disorder to restore the nigro-neostriatal hypofunction by increasing the post synaptic dopamine receptor stimulation. However, when a dopamine agonist such as L-DOPA is used to treat Parkinson's disease, typically, dyskinesias occur in the patient as a side effect. These dyskinesias usually occur at the peak dosage and may assume one or more of several possible forms such as choreic, dystonic, athetotic or myoponic with varying intensities and sometimes occurs to such an extent that it is worse than the underlying Parkinsonism. It is believed that the development of L-DOPA induced dyskinesias result from severe nigrostriatal denervation in combination with chronic L-DOPA treatment for a period of time of months to years. Once the dyskinesias manifest themselves, the therapeutic options that can be offered to the patient are reduced.

Freed et al in N Engl J Med, Vol. 344, No. 10, Mar. 8, 2001, pages 710–719, proposes the treatment of Parkinson's disease by transplanting human embryonic dopamine neurons into the brains of patients with Parkinson's disease as a method of raising dopamine levels in the corpus striatum and alleviating the effects associated with Parkinson's disease. This method of treatment was shown to be successful in some patients in reducing the symptoms and signs of Parkinson's disease but had problems of the development of dystonias and dyskinesias after the transplantation of the embryonic dopamine neurons, even after a substantial reduction in or elimination of therapy with dopamine-agonist drugs.

U.S. Pat. No. 5,462,947 to Svensson et al discloses substituted phenylazacycloalkanes which possess selective dopamine receptor pharmacological properties and are useful in treating central nervous system disorders such as depression symptoms, geriatric disorders, schizophrenia, narcolepsy, MBD, obesity, disturbances of sexual functions, and rehabilitation of drug abusers.

Ekesbo et al in Neuro Report, Vol. 8, No. 11, Jul. 28, 1997, pages 2567–2570, teaches the use of S-(−)-3-[3-(methylsulfonyl)phenyl]-1-propyl-piperidine attenuating L-DOPA-induced contraversive turning behavior in unilaterally dopamine-lesioned monkeys.

Ekesbo et al in Eur. J. Pharmacol. (2000), 389 (2/3), 193–199, discloses that treatment with S-(−)-3-[3-(methylsulfonyl) phenyl]-1-propyl-piperidine attenuated rotational behavior induced by apomorphine, L-DOPA and quinpirole without inducing motor impairment such as akinesia or dystonia.

Waters et al in WO 99/03470 discloses the use of specified substituted 3-phenylpiperidines and 3-phenylpyrolidine analogs for treating impaired cognitive functions for patients suffering from dementia, schizophrenia, bi-polar disease, attention deficit disorders, hyperactivity disorders and neurological disorders such as Parkinson's and Huntington's diseases.

Waters et al in WO 00/03714 discloses specific substituted 3-phenylpiperidines and 3-phenylpyrolidine analogs for the treatment of dyskinesias such as dystonias, tremor and chorea and Huntington's disease.

SUMMARY OF THE INVENTION

The present invention is directed to a method for preventing the development of and treating dyskinesias resulting from the treatment of a patient suffering from Parkinson's disease which comprises a step of administering a substituted phenylazacycloalkane compound according to formula (I).

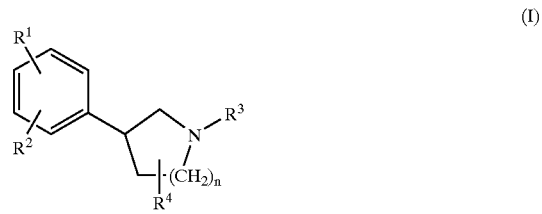

(I)

wherein n is 1 or 2; $R^1$ and $R^2$ are independently H, provided that both are not H, —OH, CN, $CH_2CN$, 2- or 4-$CF_3$, $CH_2CF_3$, $CH_2CHF_2$, CH=$CF_2$, $(CH_2)_2CF_3$, ethenyl, 2-propenyl, $OSO_2CH_3$, $OSO_2CF_3$, $SSO_2CF_3$, COR, COOR, $CON(R)_2$, $CONH_2$, $SO_xCH_3$, $SO_xCF_3$, $O(CH_2)_xCF_3$, where x is 0–2, $SO_2N(R)_2$, CH=NOR, COCOOR, $COCOON(R)_2$, $C_{1-8}$ alkyls, $C_{3-8}$ cycloalkyls, $CH_2OR$, $CH_2(R)_2$, $NRSO_2CF_3$, $NO_2$, halogen, phenyl in positions 2, 3 or 4, thienyl, furyl, pyrrole, oxazole, thiazole, N-pyrroline, triazole, tetrazole or pyridine;

$R^3$ is hydrogen, $CF_3$, $CH_2CF_3$, $C_{1-8}$ alkyl, $C_{3-8}$ cycloalkyl, $C_{4-9}$ cycloalkyl-methyl, $C_{2-8}$ alkenyl, $C_{2-8}$ alkynyl, 3,3,3-trifluoropropyl, 4,4,4-trifluorobutyl, =$(CH_2)_m$—$R^5$, where m is 1–8, $CH_2SCH_3$ or a $C_{4-8}$ alkylene bonded to the N-atom and one of its adjacent carbon atoms to form a heterocyclic structure;

$R^4$ and R are independently selected from hydrogen, $CF_3$, $CH_2CF_3$, $C_1$–$C_8$ alkyl, $C_{3-8}$ cycloalkyl, $C_{4-9}$ cycloalkyl-methyl, $C_{2-8}$ alkenyl, $C_{2-8}$ alkynyl, 3,3,3-trifluoropropyl, 4,4,4-trifluorobutyl, or —$(CH_2)_m$—$R^5$, where m is 1–8;

$R^5$ is phenyl, phenyl substituted with CN, $CF_3$, $CH_2CF_3$, $C_{1-8}$ alkyl, $C_{3-8}$ cycloalkyl, $C_{4-9}$ cycloalkyl-methyl, $C_{2-8}$ alkenyl or $C_{2-8}$ alkynyl, 2-thiophenyl, 3-thiophenyl, —$NR^6CONR^6R^7$ or $CONR^6R^7$; and $R^6$ and $R^7$ are independently hydrogen, $C_{1-8}$ alkyl, $C_{3-8}$ cycloalkyl, $C_{4-9}$ cycloalkyl-methyl, $C_{2-8}$ alkenyl or $C_{2-8}$ alkynyl.

The compounds of formula (I) can be provided in both the racemic mixtures and the pure R or S enantiomers. The preferred compounds have the S absolute configuration according to the Cahn-Ingold-Prelog priority rules and, depending on the N-substituents, may be dextrorotatory or levorotatory.

In one preferred embodiment of the present invention, the compound of formula (I) is S-(−)-3-[3-(methylsulfonyl) phenyl]-1-propyl-piperidine, which can be provided in the form of a pharmaceutically acceptable salt, such as a hydrochloride salt.

The present invention provides a method for preventing the development of dyskinesias in a patient being treated for Parkinson's disease through the use of a dopamine agonist without inducing akinesia or reducing the anti-Parkisonian efficacy of the dopamine agonist. Another aspect of the present invention provides a method for treating dyskinesias developed in a patient being treated for Parkinson's disease through the use of a dopamine agonist without reducing the anti-Parkinsonian efficacy of the dopamine agonist. The compound of formula (I) can be administered concomitantly with the dopamine agonist or before or after the administration of the dopamine agonist. "Concomitantly" is defined to mean within the same treatment period as the administration of the dopamine agonist which is preferably within twelve hours and up to forty-eight hours from the administration of the dopamine agonist. "Prevention" means preventing the appearance of dyskinesias or reducing the progression of severity of already established dyskinesias.

In another preferred embodiment of the present invention, the dopamine agonist is L-DOPA.

The present invention also provides a method for the treatment or prevention of dyskinesias in a patient treated for Parkinson's disease by the transplantation of dopamine neurons into the brain of the patient through the administration of the compound of formula (I). Patients undergoing such transplantations can also be treated with different neurotrophic factors to facilitate neuronal growth. The compound of formula (I) can be administered after the transplantation has occurred either solely or in combination with a dopamine agonist. When the compound of formula (I) is administered in combination with a dopamine agonist, it can be administered within the same treatment period as the administration of the dopamine agonist, which is preferably within twelve hours and up to forty-eight hours from the administration of the dopamine agonist.

DETAILED DESCRIPTION OF THE INVENTION

Figure 1:
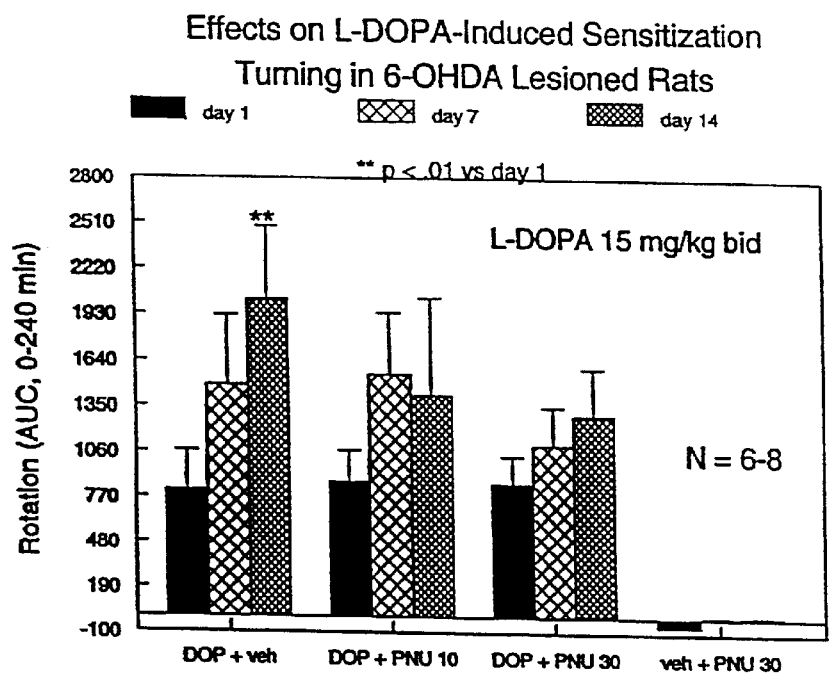
FIG. 1 illustrates the turning activity of rats treated with L-DOPA alone, S-(−)-3-[3-(methylsulfonyl) phenyl]-1-propyl-piperidine and then L-DOPA and S-(−)-3-[3-(methylsulfonyl)phenyl]-1-propyl-piperidine alone.

The substituted phenylazacycloalkanes of the present invention are described in Svensson et al, U.S. Pat. Nos. 5,462,947 and 5,594,024, the disclosures of which are incorporated herein by reference thereto.

In one aspect of the present invention, the substituted phenylazacycloalkane compounds of formula (I) are administered with the dopamine agonist prior to the onset of the dyskinesias brought on by the use of the dopamine agonist to treat Parkinson's Disease. The development of dyskinesias can be prevented through the use of the compounds of formula (I) with little if any attenuation of the anti-Parkinsonian effects of the dopamine agent.

In another aspect of the present invention, the substituted phenylazacycloalkane compounds of formula (I) are administered with the dopamine agonists after the onset of the dyskinesias brought on by the use of the dopamine agonist to treat Parkinson's Disease. The dyskinesias can be stopped or the progression of the dyskinesias to a more severe phase can be slowed or prevented completely through the use of the compounds of formula (I) with little if any attenuation of the anti-Parkinsonian effects of the dopamine agent.

In yet another aspect of the present invention, the substituted phenylazacycloalkane compounds of formula (I) is administered to a patient being treated for Parkinson's disease by the transplantation of dopamine neurons into the patient's brain to prevent the onset of dyskinesias brought on by the transplantation without attenuation of the anti-Parkinsonian effects of the transplanted neurons. The source of the dopamine neurons can be from either a human or a non-human donor. A preferred source is a human embryo. If dyskinesias have already commenced in the patient, the compounds of formula (I) can be used to stop the dyskinesias or slow the progression of the dyskinesias to a more severe phase.

In therapeutical treatment, an effective or therapeutic amount of administration of the substituted phenylazacycloalkane compound is from about 1 to 2000 mg for oral application, preferably 10 to 600 mg, and from about 0.1 to 1000 mg for parenteral application, preferentially 1.0 to 250 mg daily doses. The daily doses are preferably administered in individual dosages one to four times daily and the dosage amounts are based on an individual having a weight of 70 kg. The dosage amount of the dopamine agonist is the same as used for normal treatment of Parkinson's Disease and determined by the patient and the type of agonist.

The compounds of formula (I) can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., $15^{th}$ Ed., 1975). The compounds and compositions of the present invention can be administered parenterally (for example, by intravenous, intraperitoneal or intramuscular injection), topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. The above listing is merely representative and one skilled in the art could envision other binders, excipients, sweetening agents and the like. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices including, but not limited to, those relying on osmotic pressures to obtain a desired release profile (e.g., the OROS drug delivery devices as designed and developed by Alza Corporation)

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions. Sterilization of the powders may also be accomplished through irradiation and aseptic crystallization methods. The sterilization method selected is the choice of the skilled artisan.

The present invention is particularly effective when the dopamine agonist is L-DOPA and the compound of formula 1 is S-(−)-3-[3-(methylsulfonyl)phenyl]-1-propyl-piperidine. However, in the present invention, the substituted phenylazacycloalkane compound of formula (I) can be used with other dopamine agonists, such as apomorphine, bromocriptine, cabergoline, lisuride, pergolide, ropinirole and pramipexole, which directly stimulate the post-synaptic receptors. Monoamine oxidase B inhibitors (such as rasagiline and selegiline) and catechol-o-methyl transferase inhibitors (such as tolcapone and entacapone) are sometimes used to enhance the actions of L-DOPA. The described method also comprises the use of substituted phenylazacycloalkanes in combination with L-DOPA and monoamine oxidase B or catechol-o-methyl transferase inhibitors.

The efficacy of the present invention is shown below by the following experimental results.

Experimental Procedures

Repeated administration of dopamine agonists to 6-OH-dopamine lesioned rats results in behavioral sensitization or enhanced rotational behavior in the rats. This effect is believed to mirror the development of motor complications including L-DOPA induced involuntary movements such as dyskinesias in Parkinson's Disease patients.

Male Sprague-Dawley rats having lesion surgery were provided. The lesion was performed in rats having an initial weight of 175–225 g and pretreated with desmethylimipramine 25 mg/kg i.p. 1 hour prior to surgery. The rats were anesthetized with 60 mg/kg i.p. sodium pentobarbital and then placed in a stereotaxic apparatus. A small hole was drilled through the skull of the rats and a 30-gauge stainless tubing was lowered to the right (one study) or left (two studies) medial forebrain bundle. 8 $\mu$g/4 $\mu$L (8$\mu$ free base) of 6-OH-dopamine solution was injected into the medial forebrain bundle at a rate of 1 $\mu$L/min. Following surgery, the incision was closed with clips and ointment containing a local anesthetic/antibiotic was applied to the incision area. The rats were returned to their home cages and allowed one week to recover from surgery.

The rats were group housed in wire mesh hanging cages with free access to food and water and kept on 12-hour light:12-hour dark cycles with the light being on from 6:00 a.m. to 6:00 p.m. All behavioral testing was done between 9:00 a.m. to 6:00 p.m.

Two to three weeks after the surgery, the rats were screened to assess the degree of lesion by measuring their net turning response to a single dose of 0.1 mg/kg s.c. of apomorphine HCl in 0.9% saline. The total turns were recorded in discrete 10 minute intervals. Each rat was connected by a lightweight harness and tether to a rotometer comprising a swivel with a mechanical counter at the top of a clear plastic cylindrical cage. The rats were used for the experiments if they had at least 30 contralateral turns in 10 minutes, with contralateral being away from the side of the lesion. In addition to screening out incomplete lesions, the response to apomorphine was used to separate the rats into balanced treatment groups, prior to the start of chronic dosing. The rats were ranked by cumulative net turning response and an equal number of high and low responders were placed in each treatment group.

Figure 2:
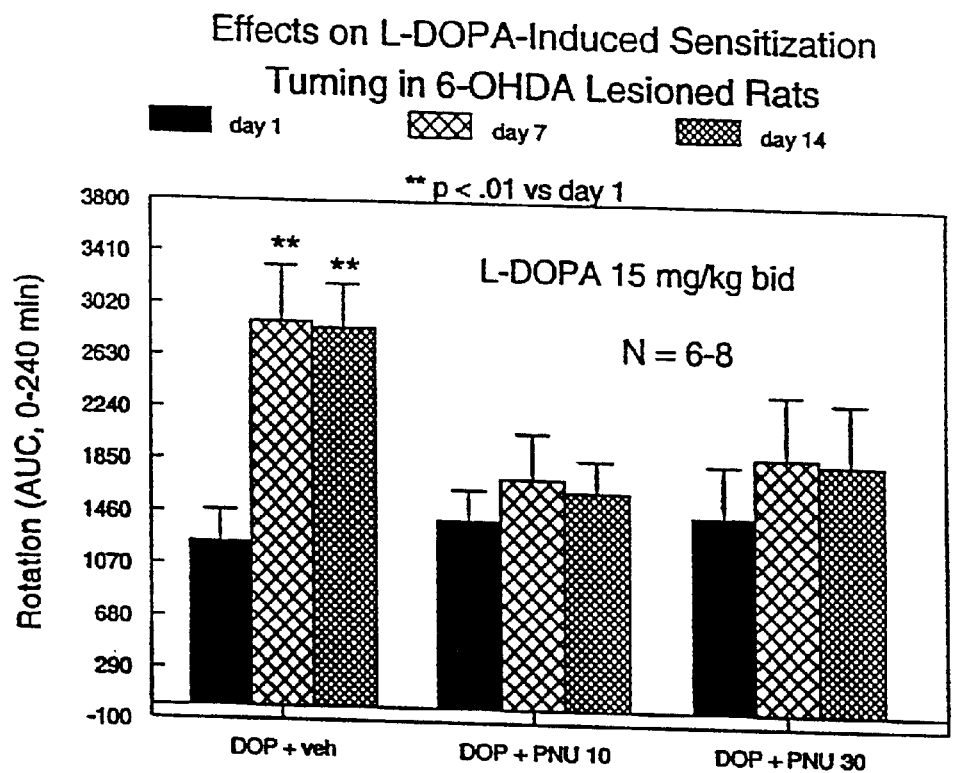
FIG. 2 illustrates the turning activity of rats treated with L-DOPA alone, and L-DOPA and S-(−)-3-[-(methylsulfonyl)phenyl]-1-propyl-piperidine concomitantly.

All of the injections were given in a volume of 2 ml/kg and, with the exception of L-DOPA+benserazide 15+5 mg/kg, i.p., all injections were subcutaneous. All chronic treatment was given bid, 6–8 hours apart. 15 mg/kg (free base) L-DOPA HCl was dissolved in 0.25% methylcellulose/water along with benserazide HCl (peripheral dopa decarboxylase inhibitor) in an amount of 5 mg/kg. S-(−)-3-[3-(methylsulfonyl)phenyl]-1-propyl-piperidine was dissolved in 0.9% sterile saline and administered at either 10 or 30 mg/kg subcutaneously 20 minutes before L-DOPA or together with the L-DOPA. The basal turning measurement started immediately after the rats received the first injections on day 1 with the activity being measured for 4–6 hours after dosing. The turning activity was measured again on days 7 and 14 and compared to the activity on day 1. The results of administering the S-(−)-3-[3-(methylsulfonyl)phenyl]-1-propyl-piperidine before treatment with the L-DOPA is illustrated in FIG. 1 while the co-administration of the S-(−)-3-[3-(methylsulfonyl)phenyl]-1-propyl-piperidine with the L-DOPA is illustrated in FIG. 2. Analysis of variance was used for statistical calculations and probability levels of <0.05 was regarded as being statistically significant.

In order to perform the brain monoamine neurochemistry analysis, the brains were harvested following 14 days of chronic drug treatment. This was performed by decapitating the rats one hour after the evening drug administration, collecting the trunk blood into EDTA-treated tubes, immediately removing the brains, freezing the brains in small aluminum pans on dry ice and then storing at −80° C. Brain levels of L-DOPA and dopamine were analyzed by means of liquid chromatography and electrochemical detection according to standard methodology described in the literature. Blood was spun and plasma was frozen at −80° C. for analysis of S-(−)-3-[3-(methylsulfonyl) phenyl]-1-propyl-piperidine and its major N-dealkylated metabolite. Plasma concentrations of S-(−)-3-[3-(methylsulfonyl)phenyl]-1-propyl-piperidine and its despropyl metabolite were quantitated using on-line high performance liquid chromatography (HPLC) tandem mass spectroscopy (MS/MS) with an atmospheric pressure chemical ionization (APCI) interface. Aliquots of water (25 $\mu$L) and an aqueous internal standard (IS) solution of [$^{13}$C, $^2$H$_3$] S-(−)-3-[3-(methylsulfonyl) phenyl]-1-propyl-piperidine (0.1 $\mu$g/mL, 25 $\mu$L) were quantitatively added to 100 $\mu$L of plasma sample. Calibration standards were prepared using 100 $\mu$L of blank plasma and substituting 25 $\mu$L of aqueous solutions of S-(−)-3-[3-(methylsulfonyl) phenyl]-1-propyl-piperidine and its major N-dealkylated metabolite for the water. The linear range of the calibration curve calculated in plasma was 0.02 nmol/mL to 40 nmol/mL for S-(−)-3-[3-(methylsulfonyl) phenyl]-1-propyl-piperidine and 00.01 nmol/mL to 20 nmol/mL for its N-dealkylated metabolite. Plasma proteins were then precipitated with the addition of 10% (w/v) aqueous trichloroacetic acid and separated by centrifugation. The resulting supernatants were transferred to polypropylene vials and injected directly onto a Phenomenx phenyl-hexyl column (2.0×150 mm, 5 $\mu$m) using a Hewlett Packard 1050 autosampler. The analytes were eluted by a Hewlett Packard 1050 quaternary pump using an isocratic mobile phase mixture of acetonitrile:methanol:0.3% v/v aqueous trifluoroacetic acid (1:3:6 v/v/v) at a constant flow rate of 0.3 mL/min. The total HPLC effluent was directed to waste from 0–2.3 min post sample injection and then introduced into a Finnigan MAT TSQ 700 triple quadrupole mass spectrometer between 2.3 and 4.5 min. Positive ion MS/MS analyses of S-(−)-3-[3-(methylsulfonyl)phenyl]-1-propyl-piperidine, its N-dealkylated metabolite, and [$^{13}$C, $^2$H$_3$] S-(−)-3-[3-(methylsulfonyl) phenyl]-1-propyl-piperidine were conducted by selected reaction monitoring (SRM). For S-(−)-3-[3-(methylsulfonyl)phenyl]-1-propyl-piperidine and the metabolite, product ions with m/z 129 arising from the collisionally induced dissociation (CID) of the protonated molecular ions of S-(−)-3-[3-(methylsulfonyl) phenyl]-1-propyl-piperidine (m/z 282) and its metabolite (m/z 240) were monitored. Product ions with m/z 173 were monitored following CID of the protonated stable isotope (m/z 286).

The retention time of the metabolite was approximately 2.6 min and for S-(−)-3-[3-(methylsulfonyl)phenyl]-1-propyl-piperidine and its stable isotope the retention time was approximately 3.2 min. Data was uploaded to the Nighthawk super computer for integration and quantitation. The ratios of analyte (S-(−)-3-[3-(methylsulfonyl)phenyl]-1-propyl-piperidine or its metabolite) and the isotope peak heights were calculated and an equation for peak height ratio as a function of concentration with a weighting function of 1/concentration was determined by least squares regression analysis. Study sample concentrations were calculated by reference to this equation.

The behavioral sensitization, measured as enhanced number of contralateral rotations, was repeatedly exhibited for L-DOPA in two separate experiments as shown in FIGS. 1 and 2. The magnitude of the behavioral sensitization was more pronounced in the second experiment as illustrated by FIG. 2. The behavioral sensitization induced by the L-DOPA was blocked by both doses of S-(−)-3-[3-(methylsulfonyl) phenyl]-1-propyl-piperidine. A timed course response evaluation for this antagonism showed that the most optimal antagonism occurred when the piperidine derivative was given simultaneously with L-DOPA, as illustrated in FIG. 2, rather than 20 minutes before the administration of L-DOPA, as shown in FIG. 1. Most importantly, in neither experiment did the piperidine derivative antagonize the basal rotational response induced by L-DOPA and the piperidine derivative did not induce rotational behavior or akinesia by itself.

Figure 3:
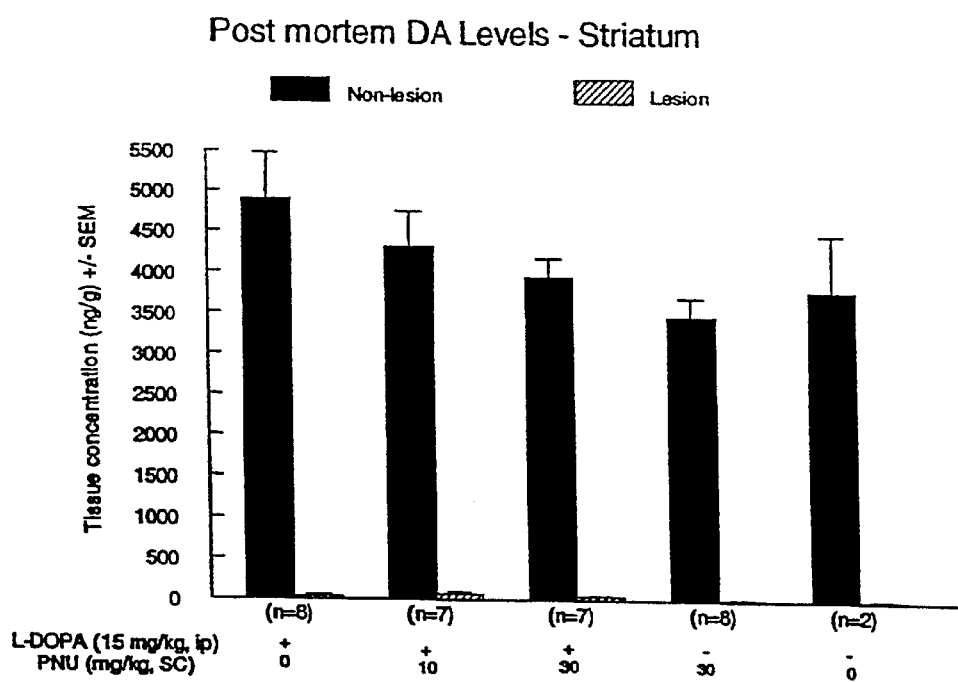
FIG. 3 illustrates the post mortem dopamine levels in lesioned and non-lesioned rats.

After two weeks of the administering of the L-DOPA and benserazide, tissues were taken post-mortem from the unilateral striatum and prefrontal cortex and analyzed for monoamines and their metabolite levels. As illustrated in FIG. 3, the lesioned striata for all groups were virtually devoid of dopamine. This neurochemically confirmed the completeness of the lesion and verified the initial behavioral screening with a single dose of 0.1 mg per kg apomorphine subcutaneously at two weeks post-lesion.

Figure 4:
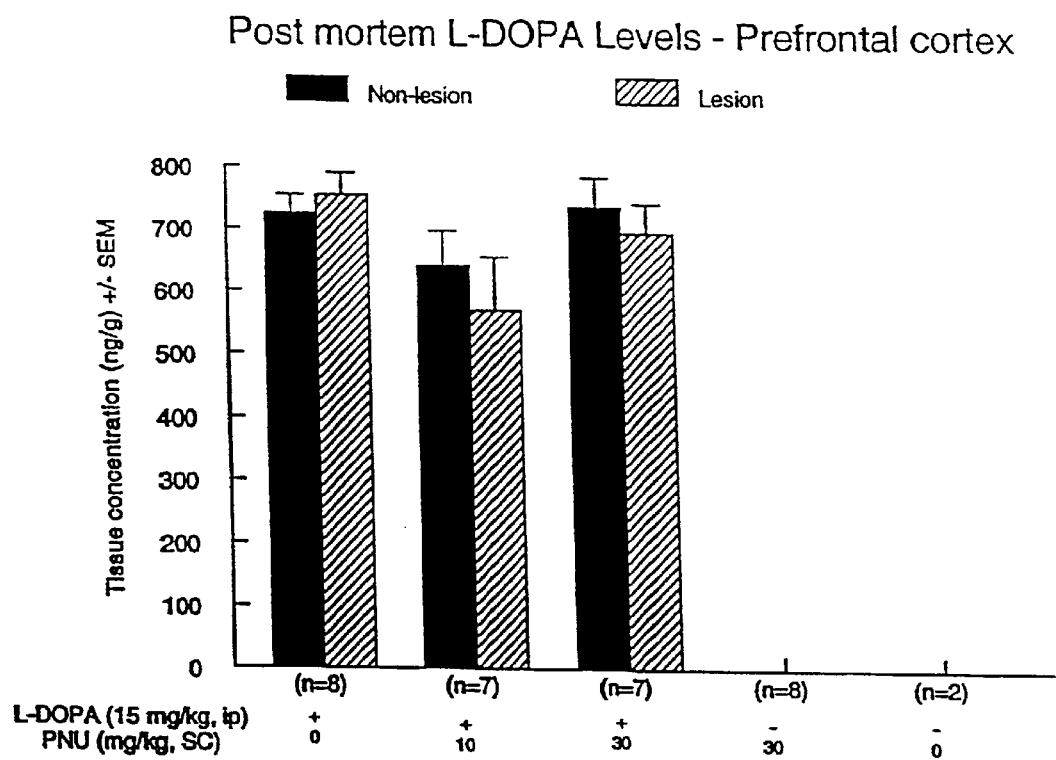
FIG. 4 illustrates the post mortem L-DOPA levels in the prefrontal cortex of lesioned and non-lesioned rats.
Figure 5:
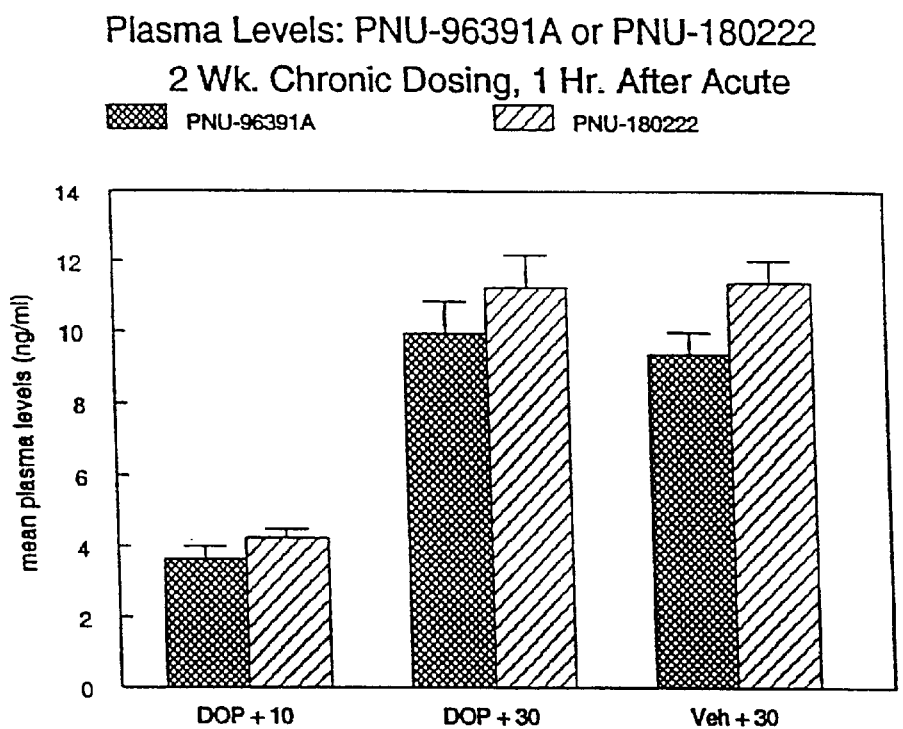
FIG. 5 illustrates the blood levels of S-(−)-3-[3-(methylsulfonyl)phenyl]-1-propyl-piperidine and its N-dealkylated metabolite after two weeks of chronic dosing.

As illustrated in FIG. 4, treatment with L-DOPA resulted in significant brain levels of this amino acid on both the lesioned and non-lesioned sides. Additionally, there was no apparent difference in the cortical levels of L-DOPA and animals treated with L-DOPA alone or L-DOPA combined with the piperidine derivative as illustrated in FIG. 4. While there was no plasma data for L-DOPA, brain L-DOPA was measured in the cortex as shown in FIG. 4. It appears that L-DOPA was uniformly entering the brain of all of the rats receiving that treatment and was evenly present on both the lesioned and non-lesioned sides. The cold treatment with the piperidine derivative did not appear to effect the brain levels of L-DOPA. As shown in FIG. 5, chronic treatment with L-DOPA did not significantly effect the blood levels of the piperidine derivative or its N-dealkylated metabolite.

The test data in the present application illustrates that the dopamine agonist L-DOPA induces rotational behavior in animals with unilateral lesions of the nigro-striatal dopamine neurons.

As shown above, the claimed substituted phenylazacycloalkanes can antagonize dopamine agonist-induced hyperactivity without inducing strong hypomotility. In addition, the substituted phenylazacycloalkanes can completely antagonize the development of behavioral sensitization induced by L-DOPA. As such, the substituted phenylazacycloalkanes can be used clinically in Parkinson's patients in combination with L-DOPA and other dopamine agonists to prevent the development of dyskinesias and other motor complications.

What is claimed is:

1. A method of preventing the development of dyskinesias in a patient being treated for Parkinson's disease by the transplantation of dopamine neurons into the patient's brain, comprising the step of administering to said patient a pharmacologically effective amount of a compound of formula (I), or a pharmaceutically acceptable salt thereof,

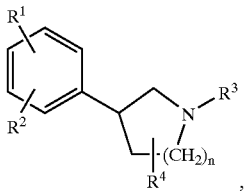

(I)

wherein n is 2; $R^1$ and $R^2$ are independently H, provided that both are not H, —OH, CN, $CH_2CN$, 2- or 4-$CF_3$, $CH_2CF_3$, $CH_2CHF_2$, CH=$CF_2$, $(CH_2)_2CF_3$, ethenyl, 2-propenyl, $OSO_2CH_3$, $OSO_2CF_3$, $SSO_2CF_3$, COR, COOR, CON$(R)_2$, $SO_xCH_3$, $SO_xCF_3$, $O(CH_2)_xCF_3$, where x is 0–2, $SO_2N(R)_2$, CH=NOR, COCOOR, COCOON$(R)_2$, $C_{1-8}$ alkyls, $C_{3-8}$ cycloalkyls, $CH_2OR$, $CH_2(R)_2$, $NRSO_2CF_3$, $NO_2$, halogen, phenyl in positions 2, 3 or 4, thienyl, furyl, pyrrole, oxazole, thiazole, N-pyrroline, triazole or tetrazole;

$R^3$ is hydrogen, $CF_3$, $CH_2CF_3$, $C_{1-8}$ alkyl, $C_{3-8}$ cycloalkyl, $C_{4-9}$ cycloalkyl-methyl, $C_{2-8}$ alkenyl, $C_{2-8}$ alkynyl, 3,3,3-trifluoropropyl, 4,4,4-trifluorobutyl, —$(CH_2)_m$—$R^5$, where m is 1–8, or $CH_2SCH_3$;

$R^4$ and R are independently selected from hydrogen, $CF_3$, $CH_2CF_3$, $C_1$–$C_8$ alkyl, $C_{3-8}$ cycloalkyl, $C_{4-9}$ cycloalkyl-methyl, $C_{2-8}$ alkenyl, $C_{2-8}$ alkynyl, 3,3,3-trifluoropropyl, 4,4,4-trifluorobutyl, or —$(CH_2)_m$—$R^5$, where m is 1–8;

$R^5$ is phenyl, phenyl substituted with CN, $CF_3$, $CH_2CF_3$, $C_{1-8}$ alkyl, $C_{3-8}$ cycloalkyl, $C_{4-9}$ cycloalkyl-methyl, $C_{2-8}$ alkenyl or $C_{2-8}$ alkynyl, 2-thiophenyl, 3-thiophenyl, —$NR^6CONR^6R^7$ or $CONR^6R^7$; and $R^6$ and $R^7$ are independently hydrogen, $C_{1-8}$ alkyl, $C_{3-8}$ cycloalkyl, $C_{4-9}$ cycloalkyl-methyl, $C_{2-8}$ alkenyl or $C_{2-8}$ alkynyl.

2. The method of claim 1, wherein said compound is (S)-(−)-3-methylsulfonylphenyl-1-propylpiperidine.

3. The method of claim 1, wherein said compound of formula (I) is administered in an amount of from 1–2000 mg.

4. The method of claim 1, wherein said compound of formula (I) is administered in an amount of from 1.0–600 mg.

5. A method of preventing the development of dyskinesias in a patient being treated for Parkinson's disease by the transplantation of dopamine neurons into the patient's brain, comprising the step of administering to said patient a pharmacologically effective amount of a compound of formula (I), or a pharmaceutically acceptable salt thereof, and a dopamine agonist

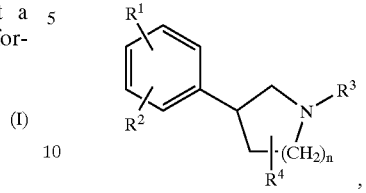

(I)

wherein n is 2; $R^1$ and $R^2$ are independently H, provided that both are not H, —OH, CN, $CH_2CN$, 2- or 4-$CF_3$, $CH_2CF_3$, $CH_2CHF_2$, CH=$CF_2$, $(CH_2)_2CF_3$, ethenyl, 2-propenyl, $OSO_2CH_3$, $OSO_2CF_3$, $SSO_2CF_3$, COR, COOR, CON$(R)_2$, $SO_xCH_3$, $SO_xCF_3$, $O(CH_2)_xCF_3$, where x is 0–2, $SO_2N(R)_2$, CH=NOR, COCOOR, COCOON$(R)_2$, $C_{1-8}$ alkyls, $C_{3-8}$ cycloalkyls, $CH_2OR$, $CH_2(R)_2$, $NRSO_2CF_3$, $NO_2$, halogen, phenyl in positions 2, 3 or 4, thienyl, furyl, pyrrole, oxazole, thiazole, N-pyrroline, triazole or tetrazole;

$R^3$ is hydrogen, $CF_3$, $CH_2CF_3$, $C_{1-8}$ alkyl, $C_{3-8}$ cycloalkyl, $C_{4-9}$ cycloalkyl-methyl, $C_{2-8}$ alkenyl, $C_{2-8}$ alkynyl, 3,3,3-trifluoropropyl, 4,4,4-trifluorobutyl, —$(CH_2)_m$—$R^5$, where m is 1–8, or $CH_2SCH_3$;

$R^4$ and R are independently selected from hydrogen, $CF_3$, $CH_2CF_3$, $C_1$–$C_8$ alkyl, $C_{3-8}$ cycloalkyl, $C_{4-9}$ cycloalkyl-methyl, $C_{2-8}$ alkenyl, $C_{2-8}$ alkynyl, 3,3,3-trifluoropropyl, 4,4,4-trifluorobutyl, or —$(CH_2)_m$—$R^5$, where m is 1–8;

$R^5$ is phenyl, phenyl substituted with CN, $CF_3$, $CH_2CF_3$, $C_{1-8}$ alkyl, $C_{3-8}$ cycloalkyl, $C_{4-9}$ cycloalkyl-methyl, $C_{2-8}$ alkenyl or $C_{2-8}$ alkynyl, 2-thiophenyl, 3-thiophenyl, —$NR^6CONR^6R^7$ or $CONR^6R^7$; and $R^6$ and $R^7$ are independently hydrogen, $C_{1-8}$ alkyl, $C_{3-8}$ cycloalkyl, $C_{4-9}$ cycloalkyl-methyl, $C_{2-8}$ alkenyl or $C_{2-8}$ alkynyl.

6. The method of claim 5, wherein said compound is (S)-(−)-3-methylsulfonylphenyl-1-propylpiperidine.

7. The method of claim 5, wherein said compound of formula (I) is administered in an amount of from 1–2000 mg.

8. The method of claim 5, wherein said compound of formula (I) is administered in an amount of from 1.0–600 mg.

9. The method of claim 5, wherein the compound of formula (I) is administered prior to the administration of the dopamine agonist.

10. The method of claim 5, wherein the compound of formula (I) is administered after the administration of the dopamine agonist.

* * * * *

UNITED STATES PATENT AND TRADEMARK OFFICE
CERTIFICATE OF CORRECTION

PATENT NO.     : 6,670,378 B2
DATED          : December 30, 2003
INVENTOR(S)    : Kjell A. Svensson It is certified that error appears in the above-identified patent and that said Letters Patent is hereby corrected as shown below:

Column 10,
Line 24, change "$c_{1-8}$ alkyl" to -- $C_{1-8}$ alkyl --
Line 29, change "$C_1$-$C_8$ alkyl" to -- $C_1$-$C_8$ alkyl --

Signed and Sealed this

Twenty-second Day of June, 2004

JON W. DUDAS
*Acting Director of the United States Patent and Trademark Office*